United States Patent
Mather et al.

(10) Patent No.: US 7,091,297 B2
(45) Date of Patent: Aug. 15, 2006

(54) SHAPE MEMORY POLYMERS BASED ON SEMICRYSTALLINE THERMOPLASTIC POLYURETHANES BEARING NANOSTRUCTURED HARD SEGMENTS

(75) Inventors: Patrick T. Mather, Storrs, CT (US); Qing Ge, Coventry, CT (US); Changdeng Liu, Storrs, CT (US)

(73) Assignee: The University of Connecticut, Farmington, CT (US)

( * ) Notice: Subject to any disclaimer, the term of this patent is extended or adjusted under 35 U.S.C. 154(b) by 0 days.

(21) Appl. No.: 10/683,167

(22) Filed: Oct. 10, 2003

(65) Prior Publication Data

US 2004/0116641 A1 Jun. 17, 2004

Related U.S. Application Data

(60) Provisional application No. 60/488,590, filed on Jul. 18, 2003, provisional application No. 60/488,323, filed on Jul. 18, 2003, provisional application No. 60/466,401, filed on Apr. 29, 2003, provisional application No. 60/419,506, filed on Oct. 18, 2002, provisional application No. 60/418,023, filed on Oct. 11, 2002.

(51) Int. Cl.
C08G 18/32 (2006.01)
C08G 18/38 (2006.01)
C08G 18/64 (2006.01)
C08G 18/76 (2006.01)
C08G 18/40 (2006.01)

(52) U.S. Cl. .................. 528/28; 524/404; 524/424; 524/428; 524/433; 524/434; 524/437; 524/442; 524/444; 524/445; 525/424; 528/73; 528/74

(58) Field of Classification Search ............... 524/404, 524/424, 428, 433, 434, 437, 442, 444, 445; 525/424; 528/28, 73, 74
See application file for complete search history.

(56) References Cited

U.S. PATENT DOCUMENTS

| | | | |
|---|---|---|---|
| 3,383,336 A | 5/1968 | Kuyama et al. | |
| 3,459,725 A | 8/1969 | Natta et al. | |
| 3,563,973 A | 2/1971 | Arditti et al. | |
| 4,612,241 A | 9/1986 | Howard, Jr. | |
| 5,145,935 A | 9/1992 | Hayashi | |
| 5,147,385 A | 9/1992 | Beck et al. | |
| 5,163,952 A | 11/1992 | Froix | |
| 5,189,110 A | 2/1993 | Ikematu et al. | |
| 5,258,020 A | 11/1993 | Froix | |
| 5,282,854 A | 2/1994 | Yagi et al. | 623/6 |
| 5,395,882 A | 3/1995 | Siol et al. | |
| 5,506,300 A | 4/1996 | Ward et al. | |
| 5,607,467 A | 3/1997 | Froix | |
| 5,665,822 A | 9/1997 | Bitler et al. | |
| 5,674,242 A | 10/1997 | Phan et al. | |
| 5,769,883 A | 6/1998 | Buscemi et al. | |
| 5,880,240 A | 3/1999 | Tsuno | |
| 5,889,118 A | 3/1999 | Delgado et al. | 525/228 |
| 5,908,918 A | 6/1999 | Chen et al. | |
| 5,910,357 A | 6/1999 | Hachisuka et al. | |
| 5,954,744 A | 9/1999 | Phan et al. | |
| 5,955,559 A * | 9/1999 | Handlin et al. | 528/63 |
| 5,964,744 A | 10/1999 | Balbierz et al. | |
| 6,024,764 A | 2/2000 | Schroeppel | |
| 6,086,204 A | 7/2000 | Magnante | |
| 6,156,842 A | 12/2000 | Hoenig et al. | |
| 6,160,084 A | 12/2000 | Langer et al. | |
| 6,217,609 B1 | 4/2001 | Haverkost | |
| 6,248,129 B1 | 6/2001 | Froix | |
| 6,368,346 B1 | 4/2002 | Jadhav | |
| 6,388,043 B1 | 5/2002 | Langer et al. | |
| 6,395,038 B1 | 5/2002 | Schroeppel | |
| 6,530,950 B1 | 3/2003 | Alvarado et al. | |
| 6,538,089 B1 | 3/2003 | Samra et al. | 526/307.4 |
| 6,679,605 B1 | 1/2004 | Zhou et al. | 351/159 |
| 6,720,402 B1 | 4/2004 | Langer et al. | |
| 6,852,825 B1 | 2/2005 | Lendlein et al. | |
| 6,858,680 B1 | 2/2005 | Gunatillake et al. | |
| 2002/0007222 A1 | 1/2002 | Desai | |
| 2002/0015519 A1 | 2/2002 | Tokas et al. | |
| 2002/0137864 A1 | 9/2002 | Tong | |
| 2003/0060793 A1 | 3/2003 | Topolkaraev et al. | |
| 2003/0191276 A1 | 10/2003 | Lendlein et al. | |
| 2004/0014929 A1 | 1/2004 | Lendlein et al. | |
| 2004/0015187 A1 | 1/2004 | Lendlein et al. | 660/228 |
| 2004/0015261 A1 | 1/2004 | Hofmann et al. | |

(Continued)

FOREIGN PATENT DOCUMENTS

EP      0 343 442      5/1989

(Continued)

OTHER PUBLICATIONS

Fu et al., "Structural Development During Deformation of Polyurethane Containing Polyhedral Oligomeric Silsesquioxanes (POSS) Molecules", *Polymer*, Vo. 42, 2001, pp. 599-611.

(Continued)

*Primary Examiner*—Rabon Sergent
(74) *Attorney, Agent, or Firm*—Cantor Colburn LLP

(57) ABSTRACT

Thermoplastic polyurethanes having an alternating sequence of hard and soft segments in which a nanostructured polyhedral oligomeric silsesquioxane diol is used as a chain extender to form a crystalline hard segment constituting SMPs. The polyurethanes are formed by reacting a polyol, a chain extender dihydroxyl-terminated POSS and a diisocyanate. The polyurethanes have multiple applications including for example, implants for human health care, drug delivery matrices, superabsorbant hydrogels, coatings, adhesives, temperature and moisture sensors, etc.

20 Claims, 3 Drawing Sheets

U.S. PATENT DOCUMENTS

| | | |
|---|---|---|
| 2004/0024143 A1 | 2/2004 | Lendlein et al. |
| 2004/0030062 A1 | 2/2004 | Mather et al. |

FOREIGN PATENT DOCUMENTS

| | | |
|---|---|---|
| EP | 0 368 274 | 11/1989 |
| EP | 0 385 443 | 2/1990 |
| EP | 0 422 693 | 2/1991 |
| EP | 0 422 693 | 4/1991 |
| EP | 1 000 958 | 11/1998 |
| WO | WO 94/14890 | 7/1994 |
| WO | WO 95/26762 | 10/1995 |
| WO | WO 99/42147 | 8/1999 |
| WO | WO 99 42528 | 8/1999 |
| WO | WO 99/46327 | 9/1999 |
| WO | WO 00/10485 | 3/2000 |
| WO | WO 00/71554 | 11/2000 |
| WO | WO 01/07499 | 2/2001 |
| WO | WO 01/10871 | 2/2001 |
| WO | WO 01/91822 | 12/2001 |
| WO | WO 02/39875 | 5/2002 |
| WO | WO 02/059170 | 8/2002 |
| WO | WO 02/083786 | 10/2002 |
| WO | WO 03/035743 | 5/2003 |
| WO | WO 03/084490 | 10/2003 |
| WO | WO 03/084491 | 10/2003 |
| WO | WO 03/088818 | 10/2003 |
| WO | WO 2003/093341 | 11/2003 |
| WO | WO 2004/006885 | 1/2004 |
| WO | WO 2004/011525 | 2/2004 |
| WO | WO 2004/032799 | 4/2004 |
| WO | WO 2004/033515 | 4/2004 |
| WO | WO 2004/033539 | 4/2004 |
| WO | WO 2004/033553 | 4/2004 |
| WO | WO 2005/009523 | 2/2005 |
| WO | WO 2005/070988 A1 | 8/2005 |

OTHER PUBLICATIONS

JP 02255830 Abstract Only; Oct. 16, 1990 (1 page).
JP 02274526 Abstract Only; Nov. 8; 1990 (1 page).
JP 11154420 Abstract Only; Jun. 8, 1999 (1 page).
JP 11302493 Abstract Only; Nov. 2, 1999 (1 page).
JP 2232212 Abstract Only; Sep. 14, 1990 (1 page).
JP 2258817 Abstract Only; Oct. 19, 1990 (1 page).
JP 3068610 Abstract Only; Mar. 25, 1991 (1 page).
JP 3068611 Abstract Only; Mar. 25, 1991 (1 page).
JP 4100831 Abstract Only; Apr. 2, 1992 (1 page).
JP 62192440 Abstract Only; Aug. 24, 1987 (1 page).
JP 61231051 Abstract Only; Oct. 15, 1986 (1 page).
JP 63145325 Abstract Only; Jun. 17, 1988 (1 page).
JP 63179955 Abstract Only; Jul. 23, 1988 (1 page).
JP 8301952 Abstract Only; Nov. 19, 1996 (1 page).
JP 9235329 Abstract Only; Sep. 9, 1997 (1 page).
JP 2000319423 Abstract Only; Nov. 21, 2000 (1 page).
Liu, et al., "Chemically Cross-Linked Polycylooctene: Synthesis, Characterization and Shape Memory Behavior" Macromolecules, (2002), 35, pp. 9868-9874.
Dinger, et al., "High Turnover Numbers with Ruthenium-Based Metathesis Catalysts" Advanced Synthesis Catalysis, vol. 344 (2002) pp. 671-677.
Oh et al., "Dynamic Mechanical Properties of Carbon Black Filled Trans-polyoctenamer Vulcanizates" (Oct. 19, 1985) Abstract Only, 1 page.
Lendlein et al., Biodegradable, Elastic Shape-Memory Polymers for Potential Biomedical Applications, Science (2002) 296, pp. 1673-1676.
Nakayama, K., "Properties and Applications of Shape-Memory Polymers", International Polymer Science and Technology 1991, 18, T/43-48.
Irie, M., Shape Memory Polymers, Cambridge University Press: Cambridge, UK 1998, pp. 203-219.
Boochathum et al., Vulcanization of Cis- and Trans-Polyisoprene and Their Blends: Crystallization Characteristics and Properties, European Polymer Journal, 37 (2001) pp. 429-434.
Boochathum et al., "Vulcanization of Cis- and Trans-Polyisoprene and Their Blends: Cure Characteristics and Crosslink Distribution", European Polymer Journal 37 (2001) pp. 417-427.
Schwab et al., "Synthesis and Applications of $RuCl_2(=CHR')(PR_3)_2$: The Influence of the Alkylidene Moiety on Metathesis Activity", J. Am. Chem. Soc. (1996) 118, pp. 100-110.
Bielawski et al., "Highly Efficient Ring-Opening Metathesis Polymerization (ROMP) Using New Ruthenium Catalysts Containing N-Heterocyclic Carbene Ligands", Angew. Chem. Int. Ed. (2000) 39, No. 16, pp. 2903-2906.
Calderon et al., "Melting Temperature of trans-Polyoctenamer", Journal of Polymer Science: Part A-2, vol. 5, (1967), pp. 1283-1292.
Natta et al., "The Monoclinic Structure of Even trans-Polyalkenamers", European Polymer Journal, vol. 3 (1967) pp. 339-352.
Bassi et al., "The Triclinic Structure of trans-Polyoctenamer", European Polymer Journal, vol. 4, (1968), pp. 123-132.
Schneider et al., "Crystallinity of trans-Polyoctenamer: Characterization and Influence of Sample History", Journal of Molecular Catalysis, 46 (1988), pp. 395-403.
Yeh et al., "Radiation-Induced Crosslinking: Effect on Structure of Polyethylene", Colloid & Polymer Sci. 263 (1985), pp. 109-115.
Fu et al., "Nanoscale Reinforcement of Polyhedral Oligomeric Silsesquioxane (POSS) in Polyurethane Elastomer", Polymer Int. 49 (2000) pp. 437-440.
Qing Ge and Patrick T. Mather, "Synthesis of Thermoplastic Polyurethanes Bearing Nanostructured Hard Segments: New Shape Memory Polymers" Polymer Program, Institute of Materials Science and Department of Engineering, UCONN, (Jul. 2003), (Abstract, 2 pages).
Du Prez, F. E. et al., "Segmented Networks by Cationic Polymerization: Design and Applications" NATO Sci. Ser., Ser. E, (1999), pp. 75-98.
Goethals et al. "Poly(Vinyl Ethers) as Building Blocks for New Materials" Macromol. Symp., (1998), 132, pp. 57-64.
Kagami et al., "Shape Memory Behaviors of Crosslinked Copolymers Containing Stearyl Acrylate" Macromol. Rapid. Commun., (1996), 17(8), pp. 539-543.
Kaneko et al., "Shape Memory Gels with Multi-Stimuli-Responses", Proc. SPIE-Int. Soc. Opt. Eng., (1999) 3669, pp. 199-208.
Reyntjens et al., "Polymer Networks Containing Crystallizable Poly(octadecyl vinyl ether) Segments for Shape-Memory Materials", Macromol. Rapid. Commun., (1999), 20(5), pp. 251-255.
H. G. Jeon et al., "Shape Memory and Nanostructure in Poly(norbornyl-POSS) Copolymers", Polymer International, 49, (2000), pp. 453-457.
P. T. Mather et al., "Strain Recovery in Drawn POSS Hybrid Thermoplastics," XIIIth International Congress on Rheology, Cambridge, UK (2000), 4, pp. 53-55.
P. T. Mather et al., "Strain Recovery in POSS Hybrid Thermoplastics," Polymer Preprints 41(1), (2000), pp. 528-529.
Lendlein et al., "AB-Polymer Networks Based on Oligo(ε-caprolactone) Segments Showing Shape-Memory Properties" Proc. Natl. Acad. Sci., USA (2001), 98(3), pp. 842-847.
Wei et al., "Shape-Memory Materials and Hybrid Composites for Smart Systems", Journal of Materials Science 33, (1998) pp. 3743-3762.
Van Humbeeck, "Shape Memory Alloys: A Material and a Technology", Advanced Engineering Materials, vol. 3, No. 11, (2001) pp. 837-850.
Byung Kyu Kim et al., "Polyurethane Ionomers Having Shape Memory Effects", Polymer, vol. 39, No. 13 (1998), pp. 2803-2808.
Lin et al., "Study on Shape-Memory Behavior of Polyether-Based Polyurethanes. I. Influence of the Hard-Segment Content", Journal of Applied Polymer Science, vol. 69, (1998), pp. 1563-1574.
Lin et al., "Study on Shape-Memory Behavior of Polyether -Based Polyurethanes. II. Influence of Soft-Segment Molecular Weight", Journal of Applied Polymer Science, vol. 69, (1998), pp. 1575-1586.
Chun et al., "Enhanced Dynamic Mechanical and Shape-Memory Properties of a Poly(ethylene terephthalate)-Poly(ethylene glycol)

Copolymer Crosslinked by Maleic Anhydride", Journal of Applied Polymer Science, vol. 83, (2002) pp. 27-37.

Gajria et al., "Miscibility and Biodegradability of Blends of Poly(Lactic Acid) and Poly(Vinyl Acetate)", Polymer, vol. 37, (1996), pp. 437-444.

Ishii, M. "Shape Memory Resins", Trans-polyisoprene-based Shape Memory Resins, Zairyo Gijutsu (1989), 7(6), Abstract Only, 1 page.

Lendlein, Andreas and Steffen Kelch, "Shape-Memory Polymers", Angew. Chem. Int. Ed. 41, (2002), pp. 2034-2057.

Ingrid A. Rousseau and Patrick T. Mather, "Shape Memory Effect Exhibited by Smectic-C Liquid Crystalline Elastomers" J. Am. Chem. Soc., 125, (2003), pp. 15300-15301.

Liu et al., "Shape Memory of Hydrogen-Bonded Polymer Network/ Poly(ethylene glycol) Complexes", Chengdu Institute of Organic Chemistry, Chinese Academy of Sciences, Dec. 30, 2003 (5 pages).

Jeong et al., "Miscibility and Shape Memory Property of Poly(vinyl chloride)/Thermoplastic Polyurethane Blends", Journal of Materials Science 36 (2001) 5457-5463.

Jeong et al., "Miscibility and Shape Memory Effect of Thermoplastic Polyurethane Blends with Phenoxy Resin", European Polymer Journal 37 (2001) 2245-2252.

Zhu, G. et al., "Shape-Memory Effects of Radiation Crosslinked Poly($\epsilon$-caprolactone)", Journal of Applied Polymer Science, vol. 90, 1589-1595 (2003).

Yoshida et al., "Development and Application of Shape-Memory Polymer Gel (Part I)-Synthesis and Processing of Shape-Memory Polymer Gel", Hokkaidoritsu Kogyo Shikenjo Hokoku (1999), 298 Abstract Only, 1 page.

"Silsesquioxanes, Bridging the Gap Between Polymers & Ceramics" ChemFiles vol. 1, No. 6 (2001) (14 pgs).

Ramanathan et al., "Polyurethane Urea", Polymer Data Handbook, New York: Oxford University Press (1999), pp. 878-881.

Ramanathan et al., "Polyurethane Elastomers", Polymer Data Handbook, New York: Oxford University Press (1999), pp. 874-877.

Ramanathan et al., "Polyurethane", Polymer Data Handbook, New York: Oxford University Press (1999), pp. 870-873.

Sung et al., "Properties of Segmented Poly(urethaneureas) Based on 2,4-Toluene Diisocyanate. 1. Thermal Transitions, X-ray Studies, and Comparison with Segmented Poly(urethanes)", Macromolecures, 13, (1980), pp. 111-116.

Gupta et al., "Effect of Solvent Exposure on the Properties of Hydroxy-Terminated Polybutadiene-Based Polyurethanes", Polym Int, 52, (2003), pp. 938-948.

Bielawski et al., "Highly Efficient Syntheses of Acetoxy- and Hydroxy-Terminated Telechelic Poly(butadiene)s Using Ruthenium Catalysts Containing N-heterocyclic Ligands", Polymer, 42, (2001), pp. 4939-4945.

Sarbu et al., "Synthesis of Hydroxy-Telechelic Poly(methyl acrylate) and Polystyrene by Atom Transfer Radical Coupling", Macromolecules, 37, (2004), pp. 9694-9700.

Mauler et al., Liquid-Crystalline Polyacrylate Crosslinked with $\alpha$, $\omega$ Polyisoprene Diacrylate Segments, Polymer Bulletin, 41, (1998) pp. 291-297.

Sartomer Product Bulletin, "Hydroxyl Terminated Polybutadiene Resins and Derivatives-Poly bd and Krasol" Sep. 2004, 40 pages.

Wache et al., "Development of a Polymer Stent with Shape Memory Effect as a Drug Delivery System", Journal of Materials Science: Materials in Medicine, 14, (2003), pp. 109-112.

Valimaa et al., "Viscoelastic Memory and Self-Expansion of Self-Reinforced Bioabsorbable Stents", Biomaterials, 23, (2002), pp. 3575-3582.

"Suite of Shape-Memory Polymers", Chemical & Engineering, Feb. 5, 2001, 1 page.

Woojin Lee, "Polymer Gel Based Actuator: Dynamic Model of Gel for Real Time Control", Massachusetts Institute of Technology, Department of Mechanical Engineering, May 1996, 120 pages.

Brochure, Degussa High Performance Polymers, The Rubber with Unique Properties, Vestenamer©, Undated, 12 pages.

Gordon, "Applications of Shape Memory Polyurethanes", Proceedings of the First International Conference on Shape Memory and Superelastic Technologies, SMST International Committee, (1994), pp. 115-199.

Liu et al., "Thermomechanical Characterization of a Novel Series of Shape Memory Polymers", SPE ANTEC Proceedings, (2002) 5 pages.

WO9746633 Abstract Only; Dec. 11, 1997 (1 page).

WO0046262 Abstract Only; Aug. 10, 2000 (1 page).

EP0343442 Abstract Only; Nov. 29, 1989 (1 page).

Schwab et al., "Hybrid Nanoreinforced Polyurethanes Based on Polyhedral Oligomeric Silsesquioxanes (POSS)"; Rapra Abstracts; Pergamon Press Ltd., Oxford, GB, vol. 77, No. 6, Jun. 1999 (Abstract Only) (2 pages).

Schwab et al. Hybrid Nanoreinforced Polyurethanes Based on Polyhedral Oligomeric Silsesquioxanes (POSS), Am. Chem. Soc. PMSE Prep., 1997, 77, pp. 549-550.

Haddad et al., "Hybrid Inorganic/Organic Diblock copolymers. Nanostructure in Polyhedral Oligomeric Silsesquioxane Polynorbornenes." Mat. Res. Soc. Symp. Proc. vol. 628 (2000) Materials Research Society, CC.2.6.1-CC2.6.7.

* cited by examiner

DSC traces of PLA (top) quenched from T = 180°C or (bottom) annealed at T = 110°C for 1 hr.

DSC traces for PLA/PVAc blends following annealing for 1 hour at T = 110°C. A heating rate of 10°C/min was employed. PLA wt-% is indicated with each trace.

Glass transition temperatures measured following quenching of the PLA/PVAc blends (solid points). Solid line is best fit to the Fox equation, $1/T_g = w_a/T_g^a + w_b/T_g^b$.

Tensile storage modulus versus temperature for a range of PLA/PVAc blends whose composition is indicated in the plot.

SHAPE MEMORY POLYMERS BASED ON SEMICRYSTALLINE THERMOPLASTIC POLYURETHANES BEARING NANOSTRUCTURED HARD SEGMENTS

CROSS-REFERENCE TO RELATED APPLICATIONS

This application claims the priority of Provisional Applications Ser. Nos. 60/418,023 filed Oct. 11, 2002, 60/466,40 1 filed Apr. 29, 2003; Ser. No. 60/419,506 filed Oct. 18, 2002; 60/488,590 filed Jul. 18, 2003 and 60/488,323 filed Jul. 18, 2003, each of which is incorporated herein in their entirety by reference thereto. Both application Ser. No. 10/425,451 filed Apr. 29, 2003 which claims priority from provisional application Ser. No. 60/377,544 and the claimed provisional applications are also incorporated herein by reference.

TECHNICAL FIELD

The instant disclosure relates to shape memory polymers and more particularly thermoplastic polyurethanes with an alternating sequence of hard and soft segments in which a nanostructured polyhedral oligomeric silsesquioxane diol is used as a chain extender to form a crystalline hard segment and also relates to methods for the preparation of these thermoplastic polyurethanes and to applications thereof.

BACKGROUND OF THE DISCLOSURE

Shape memory materials feature an ability to transform shape from a temporary, frozen, shape to a permanent shape when triggered by an environmental stimulus, such as heat, light, or vapor. Used creatively, these phenomena can be exploited for a wide range of applications. While both shape memory alloys (SMAs) and shape memory polymers (SMPs) show similar thermo-stimulated shape memory properties, their mechanisms of action are quite distinct. Advantages of SMAs include rapid strain recovery (within 1 second), the potential training for two-way reversible memory, and an apparent superelasticity due within the austenite phase at low temperature. In contrast, polymers intrinsically exhibit shape memory effects derived from their highly coiled constituent chains that are collectively extensible via mechanical work and this energy may be stored indefinitely, known as "shape fixing," by cooling below $T_g$ or $T_m$. The polymeric samples can later perform mechanical work and return to a stress-free state when heated above the critical temperature, mobilizing the frozen chains to regain the entropy of their coiled state. In comparison to SMAs, thermally stimulated SMPs have the advantages of: (i) large recoverable deformations in excess of several hundred percent strain; (ii) facile tuning of transition temperatures through variation of the polymer chemistry; and (iii) processing ease at low cost.

Thermally stimulated SMPs with different thermomechanical properties to function in various applications, for example as medical devices and mechanical actuators have previously been synthesized and characterized. The materials span a range of room temperature moduli, from rigid glassy materials having storage moduli of several GPa to compliant rubbers with moduli as low as tens of MPa. Moreover, the retracting (rubbery) moduli have been adjusted over the range 0.5<E<10 MPa, as prescribed by the end application. One such example is chemically crosslinked polycyclooctene (PCO), a stiff semicrystalline rubber that is elastically deformed above $T_m$ to a temporary shape that is fixed by crystallization. Fast and complete recovery of gross deformations is achieved by immersion in hot water. These SMPs have been described in Provisional Patent Application Ser. No. 60/419,506 filed Oct. 18, 2002 entitled Chemically Crosslinked Polycyclooctene, the entirety of which is incorporated herein by reference. In Provisional Patent Application Ser. No. 60/377,544 filed May 2, 2002 entitled Castable Shape Memory Polymers, the entirety of which is incorporated herein by reference, stiffer SMPs offering tunable critical temperatures and rubber modulus using a thermosetting random copolymer made of two vinyl monomers that yield controlled $T_g$ and casting-type processing are described. Such copolymers were crosslinked with a difunctional vinyl monomer (crosslinker), the concentration of crosslinker controlling the rubber modulus and thus the work potential during recovery. Besides their shape memory effects, these materials are also castable allowing for processing more complex shapes. In addition, they are optically transparent making them useful for additional applications.

The use of chemical crosslinking in both of these cases limits the types of processing possible and forever sets the equilibrium shape at the point of network formation. Therefore, miscible blends of a semicrystalline polymer with amorphous polymers have also been intensively investigated due to their attractive crystalline properties and mechanical properties. For those blends that are miscible at the molecular level, a single glass transition results, without broadening, an aspect important to shape memory. Additionally, in such miscible blends the equilibrium crystallinity (which controls the plateau modulus between $T_g$ and $T_m$ where shape fixing is performed) also changes dramatically and systematically with the blend compositions. It provides a simple route to alternative shape memory plastics; i.e. SMPs with relatively high modulus in the fixed state at room temperature, having a tunable and sharp transition, and the permanent shape can be remolded repeatedly above certain melting temperatures. These SMP blends have been described in Provisional Patent Application Ser. No. 60/466, 401 filed Apr. 29, 2003 entitled Blends of Amorphous and Semicrystalline Polymers with Shape Memory Properties, the entirety of which is incorporated herein by reference.

Microphase-separated semicrystalline thermoplastic polymers with two sharp melting transitions $T_{m2}>T_{m1}>$room temperature, where the difference of the two melting points is at least 20° C., are also good candidates for shape memory offering the advantage of melt processing above $T_{m2}$, and repeated resetting of the equilibrium shape by relaxing stress in the fluid state. Representative past examples of such polymers in this class of SMP are conventional polyurethanes whose soft domains are glassy or semicrystalline with low melting point (but higher than $T_{crit}$) and whose hard domains feature a higher melting point only exceeded during processing.

OBJECTS OF THE DISCLOSURE

It is an object of the present disclosure to provide shape memory polymers comprising hybrid polyurethanes.

It is another object of the disclosure to provide shape memory polymers having medium and tunable modulus in the fixed state at room temperature, having a tunable and sharp transition, whose permanent shape can be repeatedly remolded above a certain melting temperature.

It is another object of the disclosure to provide hybrid polyurethane SMPs evidencing sharp and tunable transition temperatures, adjustable stiffness above their transition temperatures and thermal processability above the melting point of the POSS domains.

It is yet another object of the disclosure to provide hybrid polyurethane SMPs which possess excellent shape recovery effect at the recovery temperature and wherein the retracting force is adjustable according to the composition of the POSS.

Still a further object of the disclosure is to provide hybrid polyurethanes that are biocompatible and can be used as medical devices and implants.

Yet another object of the disclosure is a method for synthesizing such hybrid polyurethanes.

SUMMARY

Broadly the disclosure provides a method for producing hybrid polyurethane SMPs by reacting (A) a polyol, (B) a chain extender dihydroxyl-terminated POSS and (C) a diisocyanate, wherein POSS stands for a polyhedral silsesquioxane diol. The polyol (A) can be polyethylene glycol (PEG), polycaprolactone (PCL) diol, polycyclooctene diol, trans-1,4 butadiene, transisoprene, polynorbornene diol and polymethacrylate copolymer. The chain extender (B) can be TMP cyclopentyldiol-POSS (2-ethyl-2-[3-[[(heptacyclopentylpentacyclo-[9.5.1.1$^{3,9}$.1$^{5,15}$.1$^{7,13}$]octasiloxanyl)oxy]dimethylsilyl]-propoxy]methyl]-1,3-propanediol, Chemical Abstracts Registry No. 268747-51-9), TMP cyclohexyldiol-POSS (2-ethyl-2-[3-[[(heptacyclohexylpentacyclo-[9.5.1.1$^{3,9}$.1$^{5,15}$.1$^{7,13}$]octasiloxanyl)oxy]dimethylsilyl]-propoxy]methyl]-1,3-propanediol), TMP isobutyldiol-POSS (2-ethyl-2-[3-[[(heptaisobutylpentacyclo-[9.5.1.1$^{3,9}$.1$^{5,15}$.1$^{7,13}$]octasiloxanyl)oxy]dimethysilyl]-propoxy]methyl]-1,3-prapanediol), trans-cyclohexanediol-cyclohexane-POSS (1-(2-trans-cyclohexanediol)ethyl-3,5,7,9,11,13,15-oyclohexanepentacyclo-[9.5.1.1$^{3,9}$.1$^{5,15}$.1$^{7,13}$]octasiloxane), or transcyclohexanediolisobutyl-POSS (1-(2-trans-cyclohexanediol)ethyl-3,5,7,9,11,13,15-isobutylpentacyclo-[9.5.1.1$^{3,9}$.1$^{5,15}$.1$^{7,13}$])octasiloxane, Chemical Abstracts Registry No. 480439-48-3). And the diisocyanate (C) can be selected from a large number of diisocyanates and is preferably 4,4' diphenyl methylene dilsocyanate (MDI). Other diisocyanates (C) that are suitable for use in the synthesis of hybrid polyurethane SMPs include: toluene-2,4-diisocyanate (TDI), toluene-2,6diisocyanate, hexamethylene-1,6-diisocyanste (HDI), isophorone diisocyanate (IPDI), and hydrogenated 4,4'-diphenylmethane diisocyanate (H12MDI).

The polyol can be semicrystalline and preferably selected from polyethylene glycol (PEG), polycaprolactone (PCL) diol, polycyclooctene diol, trans-1,4 butadiene, transisoprene or it can be amorphous in which case it can be polynorbornene diol and/or polymethacrylate copolymer.

The method for producing hybrid polyurethane SMPs and the novel hybrid polyurethanes prepared thereby are illustrated by the following non-limiting reaction schemes.

Scheme 1

HO—(CH$_2$CH$_2$O)$_n$—H +

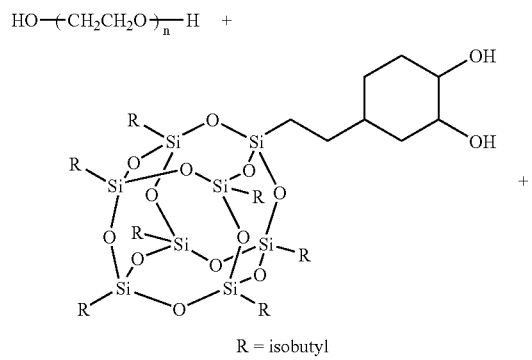

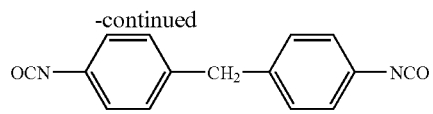

This scheme shows an example of synthesis of TPU using polyethylene glycol as polyol, trans-cyclohexanediolisbutyl-POSS as chain extender to react with 4,4' diphenyl methylene diisocyanate in toluene.

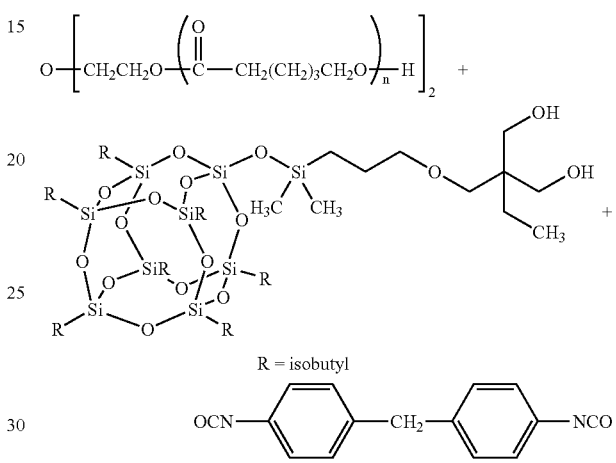

This scheme shows an example of synthesis of TPU using polycaprolactone diol as polyol, TMP Isobutyldiol-POSS as chain extender to react with 4,4' diphenyl methylene diisocyanate.

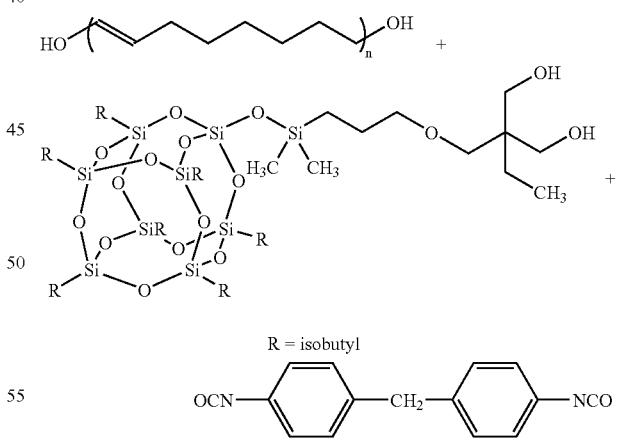

This scheme shows an example of synthesis of TPU using polycyclooctene diol as polyol, TMP Isobutyldiol-POSS as chain extender to react with 4,4' diphenyl methylene diisocyanate.

A general formula for the POSS-based TPUs incorporating PEG diol, prepared according to Scheme 1, follows. The polymers allow systematic variation in the ratio of X/Y (1 to 20), the polyol degree of polymerization (1<n<1000), and the total degree of polymerization, 2<m<100.

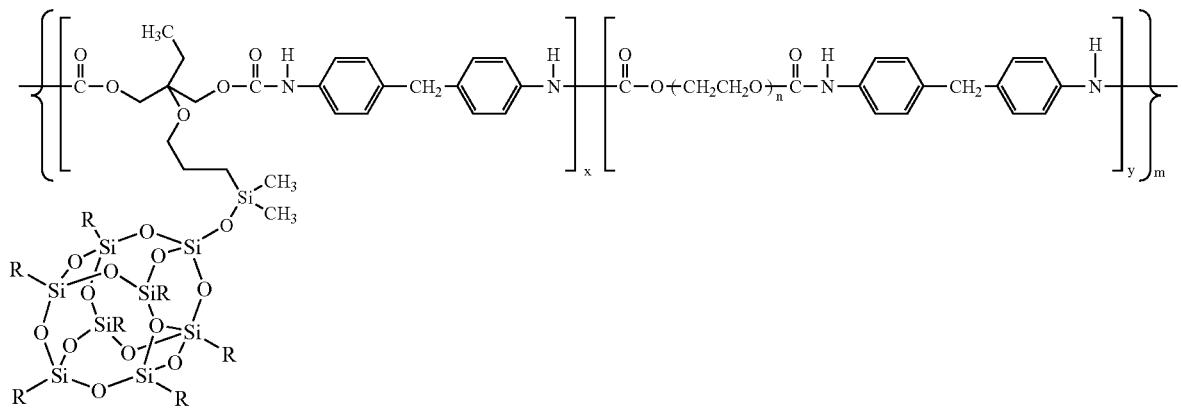

The instant hybrid polyurethanes demonstrate sharp and tunable transition temperatures, adjustable stiffness above their transition temperatures, and thermal processibilty above the melting point of the POSS domains. The hybrid polyurethanes also show excellent shape recovery effect at the recovery temperature and a retracting force which is adjustable according to the composition of the POSS. They also posses a unique property that is different from the other shape memory polymers in that the current disclosure (in the PEG embodiment) can be triggered to recover by moisture (liquid or vapor) in addition to heating. For the thermal triggering mechanism, the range 30° C. to 60° C. according to the ratio of the components used and (importantly) thermal annealing to achieve steady-state (equilibrium) crystallinity is important. The recovery can be finished within seconds when heated 20° C. above the transition temperature. The additional advantages of the materials include that the materials are rigid at room temperature, the polymers generally are biocompatible and in some cases biodegradable and can be used as medical devices and implants. The products also can be dyed to any color or rendered radio-opaque for d-ray radiography according to application requirements.

Any of the hybrid polyurethane polymers mentioned above may be filled with, for example, nanoparticles of boron nitride, silica, titanium dioxide, montmorillonite, clay, Kevlar, staple, aluminum nitride, barium and bismuth subcarbonate. Clay and silica can be used to, for example, increase the modulus of the plastic. Dispersing agents and/or compatibilizing agents may be used, for example, to improve the blending of polymers and the blending of polymers with fillers. Dispersing agents and/or compatibilizing agents include, for example, ACRAWAX® (ethylene bis-stearamide), polyurethanes and ELVALOY® (acrylic functionalized polyethylene). The polymers can be cross-linked by application of radiation such as e-beam, UV, gamma, x-ray radiation or by heat-activated chemical crosslinking techniques. Radiation techniques provide the advantage that the polymer typically does not have to be substantially heated to achieve crosslinking. For e-beam radiation, an exposure of about 200–300, e.g. 250 kilograys, typically provides sufficient crosslinking.

DETAILED DESCRIPTION

Thermoplastic polyurethanes with different compositions were synthesized by one-step condensation polymerization using the scheme shown above. Toluene was used as solvent and dibutyltin dilaurate was used as catalyst. The reaction was kept at 90° C. under the nitrogen for 2 hours and then cooled down to room temperature and precipitated into hexane. The product was dried thoroughly and dissolved in toluene to make a 10 wt % solution for casting films. The molecular weights and molecular weight distributions of this series of samples obtained from size exclusion chromatography are summarized in Table 1.

TABLE 1

Molecular weights and molecular weight distributions of POSS-based polyurethanes having polyol (PEG) block length of 10000 g/mol

| Sample | $M_n$ (g/mol) | $M_w/M_n$ |
|---|---|---|
| PEG:POSS = 1:3 | 47,400 | 1.42 |
| PEG:POSS = 1:4 | 48,800 | 1.44 |
| PEG:POSS = 1:6 | 54,000 | 1.54 |
| PEG:POSS = 1:8 | 49,200 | 1.30 |

Figure 1:
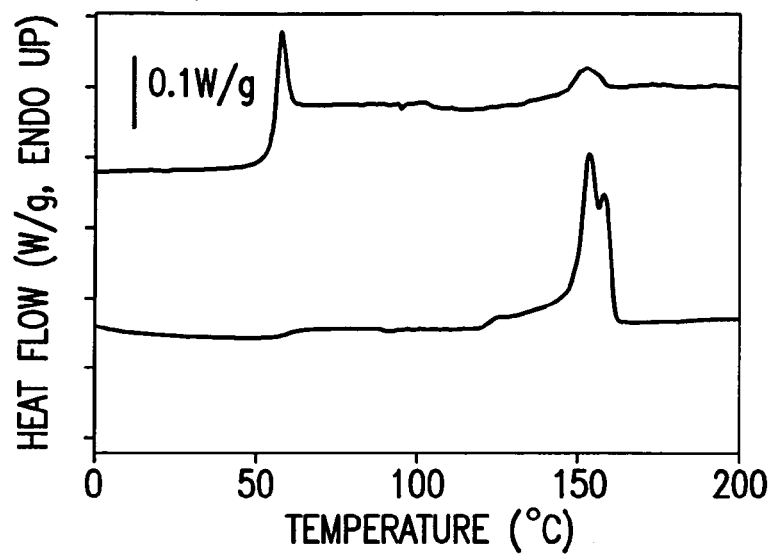
FIG. 1 illustrates graphically the DMA plots of the TMP POSS based thermoplastic polyurethane (TPU) with mole ratio of PEG: POSS as 1:6, 1:4 respectively.
Figure 2:
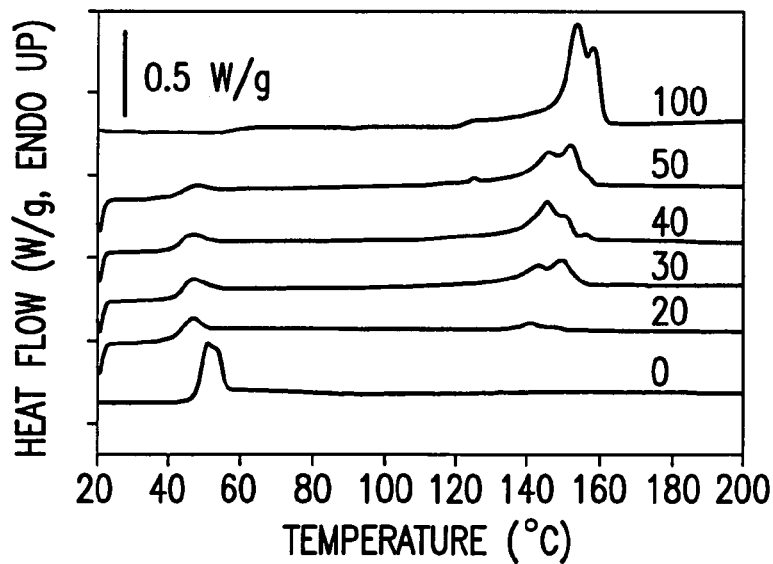
FIG. 2 illustrates graphically the DSC results of TMP POSS based TPU with different PEG:POSS mole ratios.
Figure 3:
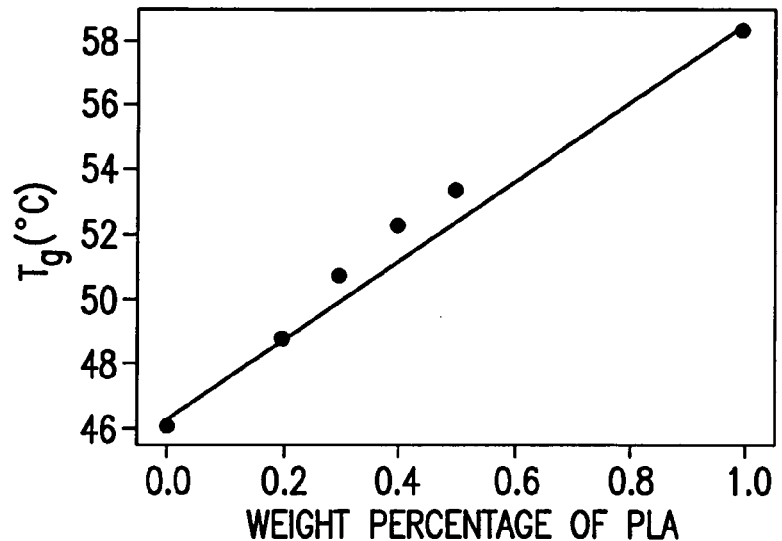
FIG. 3 illustrates the equipment as used for measuring stress-strain.
Figure 4:
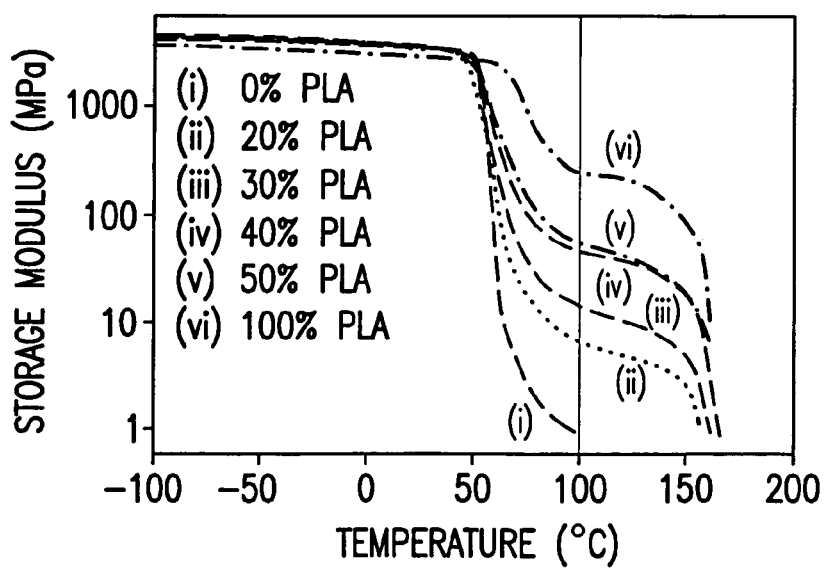
FIG. 4 illustrates graphically the stress-strain plot of the TMP POSS based TPU (PEG:POSS=1.6).
Figure 5:
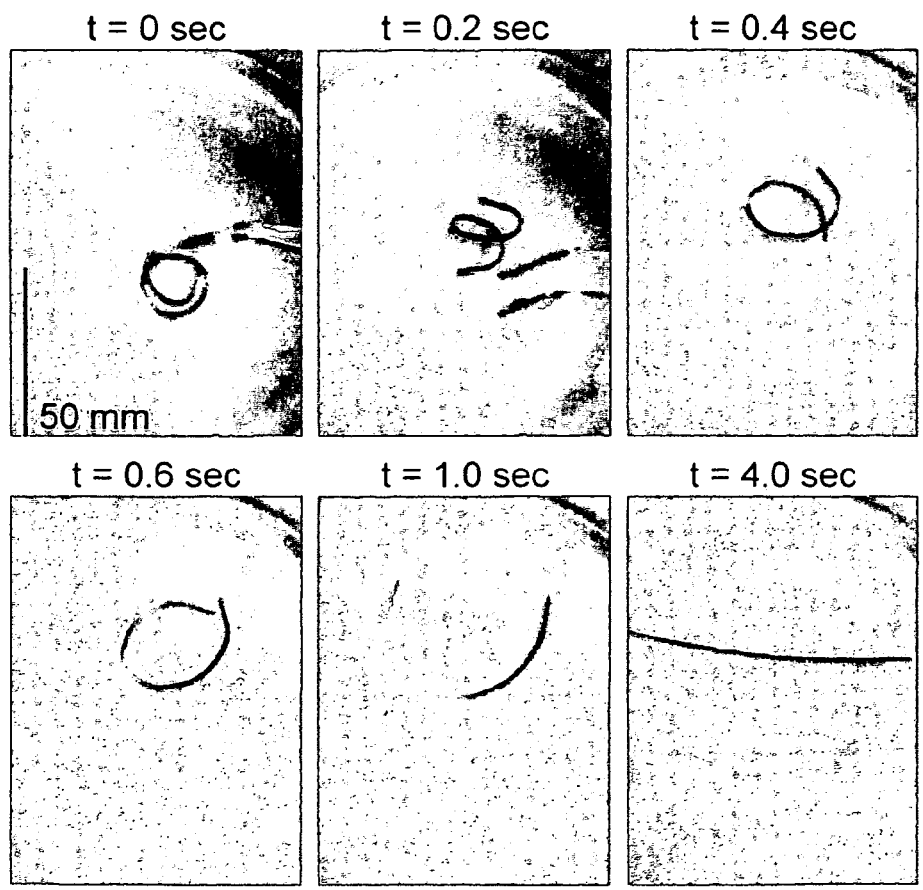
Figure 1:
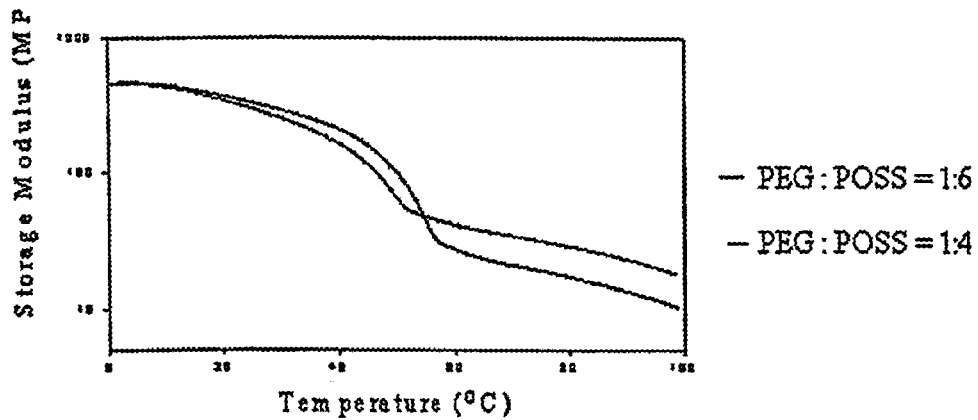
Figure 2:
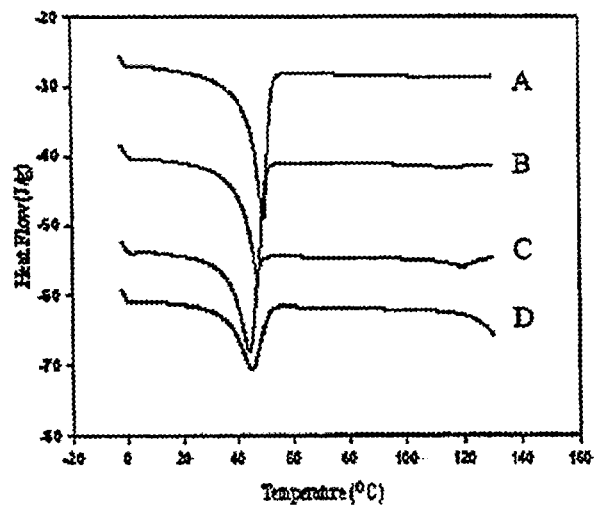
Figure 3:
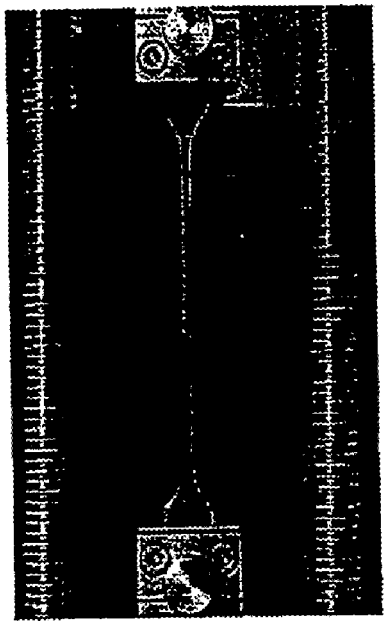
Figure 4:
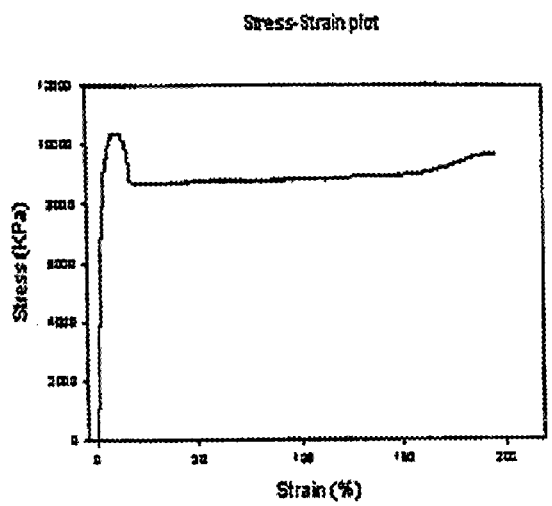

Samples of polyurethanes with different compositions were characterized by differential scanning calorimetry (TA Instruments DSC2920). All of the samples were characterized under the same conditions: two scans were performed for each sample with heating and cooling rates of 10° C./min (FIG. 2). It was observed that this series of polyurethanes exhibit two melting points, one in the range $45<T_{m1}<50°$ C. corresponding to the melting temperature of PEG "soft" block. The other melting transition appears in the range $110<T_{m2}<130°$ C., which corresponds to the melting of a POSS-reinforced hard segment phase. The melting temperature of the soft segment is observed to shift to lower values with a broadening of the melting peak while the melting temperature of the hard segment is observed to shift to higher values with a sharpening of the melting peak when the mole ratio of polyol:chain extender decreases. This result can be explained in that as the PEG:POSS ratio decreases, the resulting block copolymer will have less overall PEG content, which will directly affect the size and perfection of the crystallization of PEG blocks. Therefore, the melting temperature moves to lower values and the peak is broadened. On the contrary, the content of POSS will increase in the block copolymers, which provides for more clear aggregation of hard segments to form larger and more perfect crystals. Therefore, the melting temperature of hard segment moves to higher values while the peak is sharpened (FIG. 2).

The dried films of the formed polyurethanes were cut into thin strips for tests of temporary shape fixing and subsequent recovery, or shape memory. For example, a sample was first heated on the hot stage to 65° C., which is well above the first transition temperature but low enough to avoid melting of the elastic network of the POSS-rich phase. It was then stretched to a certain degree of elongation and cooled down to the room temperature. The deformed shape was fixed at room temperature. Finally, the deformed sample was heated up again on hot plate to 65° C. and it was observed that the sample restored to its original length completely and within seconds. A similar phenomenon was observed when water was used as a stimulus for the shape recovery except that the sample secondarily swelled to form a tough hydrogel.

The hybrid polyurethanes of the disclosure can be used for the following applications.
  a. Stents, patches and other implants for human health care
  b. Surgical tools requiring adjustable shape but high stiffness.
  c. Arbitrarily shape-adjustable structural implements, including personal care items (dinnerware, brushes, etc.) and hardware tool handles.
  d. Self healing plastics
  e. Medical devices (a dented panel is repaired by heating or plasticizing with solvent)
  f. Drug delivery matrices
  g. High-strength thermoplastic (non-crosslinked) superabsorbant hydrogels
  h. Aqueous Theological modifiers for paints, detergents and personal care products
  i. Impression material for molding, duplication, rapid prototyping, dentistry, and figure-printing.
  j. Toys
  k. Reversible Embossing for information storage
  l. Temperature and moisture sensors
  m. Safety valve
  n. Heat shrink tapes or seals
  o. Heat controlled Couplings and fasteners
  p. Large strain, large force actuators
  q. Coatings, adhesives
  r. Textiles, clothing The shape memory polymers of the disclosure are particularly suitable as biomaterials because of their low throgmogenicity, high biocompatibility, as well as unique mechanical properties. In accordance with the disclosure the shape memory polyurethanes were formulated such that the melting temperature of one segment falls within a useful temperature range for biomedical application: 37° C.–50° C.

The present disclosure provides an advantageous shape memory polymer that includes thermoplastic polyurethane shape memory polymers formed by reacting in one step a polyol, a POSS chain extender and a diisocyanate, having medium and tunable modulus in the fixed state at room temperature having a tunable sharp transition, whose permanent shape can be repeatedly remolded above a certain melting temperature.

Although the polymers and processing methodologies of the present disclosure have been described with reference to specific exemplary embodiments thereof, the present disclosure is not to be limited to such exemplary embodiments. Rather, as will be readily apparent to persons skilled in the art, the teachings of the present disclosure are susceptible to many implementations and/or applications, without departing from either the spirit or the scope of the present disclosure. Indeed, modifications and/or changes in the selection of specific polymers, polymer ratios, processing conditions, and end-use applications are contemplated hereby, and such modifications and/or changes are encompassed within the scope of the present invention as set forth in the claims which follow.

The invention claimed is:

1. A method for making a thermoplastic polyurethane shape memory polymer comprising reacting in one step (A) a polyol, (B) a polyhedral oligosilsesquioxane diol, and (C) a diisocyanate; wherein the shape memory polymer exhibits a thermal triggering temperature of 30° C. to 60° C.

2. The method of claim 1 wherein the polyhedral oligosilsesquioxane diol is a member selected from the group consisting of 2-ethyl-2-[3-[[(heptacyclopentylpentacyclo-[9.5.1.1$^{3,9}$.1$^{5,15}$.1$^{7,13}$]octasiloxanyl)oxy[dimethylsilyl]-propoxy]methyl]-1,3-propanediol, 2-ethyl-2-[3-[[(heptacyclohexylpentacyclo-]9.5.1.1$^{3,9}$.1$^{5,15}$.1$^{7,13}$]octasiloxanyl)oxy[dimethylsilyl]-propoxy]methyl]-1,3-propanediol, 2-ethyl-2-[3-[[(heptaisobutylpentacyclo-[9.5.1.1$^{3,9}$.1$^{7,13}$]octasiloxanyl)oxy]dimethylsilyl]-propoxy]methyl]-1,3-propanediol, 1-(2-trans-cyclohexanediol)ethyl-3,5,7,9,11,13,15-cyclohexanepentacyclo-[9.5.1.1$^{3,9}$.1$^{5,15}$.1$^{7,13}$]octasiloxane, and 1-(2-trans-cyclohexanediol)ethyl-3,5,7,9,11,13,15-isobutylpentacyclo-[9.5.1.1$^{3,9}$.1$^{5,15}$.$^{7,13}$]octasiloxane.

3. The method of claim 1 wherein the diisocyanate is a member selected from the group consisting of 4,4'-diphenyl methylene diisocyanate (MDI), toluene-2,4-diisocyanate (TDI), toluene-2,6diisocyanate, hexamethylene-1,6-diisocyanate (HDI), isophorone diisacyanate (IPDI), and hydrogenated 4,4'-diphenylmethane diisocyanute (H12MDI).

4. The method of claim 1 wherein the diisocyanate is 4,4'-diphenyl methylene diisocyanate.

5. A thermoplastic polyurethane shape memory polymer according to claim 1 containing a filler which is a member selected from the group consisting of boron nitride, silica, titanium dioxide, montmorillonite, clay, staple, aluminum nitride, barium subcarbonate, and bismuth subcarbonate.

6. The method of claim 1, wherein the thermoplastic polyurethane shape memory polymer exhibits a thermal triggering temperature of 37° C. to 50° C.

7. A method for making a thermoplastic polyurethane shape memory polymer comprising reacting in one step (A) a polyol, (B) polyhedral oligosilsesquioxane diol, and (C) a diisocyanate, wherein the polyol is a member selected from the group consisting of polyethylene glycol (PEG), polycaprolactone (PCL) diol, polycyclooctene diol, polynorbornene diol and polymethacrylate copolymer.

8. A method for making a thermoplastic polyurethane shape memory polymer comprising reacting in one step (A) a polyol, (B) a polyhedral oligosilsesquioxane diol, and (C) a diisocyanate, wherein the polyol is a member selected from the group consisting of polyethylene glycol, polycaprolactone diol, and polycyclooctene diol, and is semicrystalline.

9. A method for making a thermoplastic polyurethane shape memory polymer comprising reacting in one step (A) a polyol, (B) a polyhedral oligosilsesquioxane diol, and (C) diisocyanate, wherein the polyol is an amorphous diol having a Tg in the range of 20–80° C., and is a member selected from the group consisting of polynorbornene diol and polymethacrylate copolymer diol.

10. A method for making a thermoplastic polyurethane shape memory polymer comprising reacting in one step (A) a polyol, (B) a polyhedral oligosilsesquioxane diol, and (C) a diisocyanate, wherein the polyol is a member selected from the group consisting of polyethylene glycol, polycaprolactone diol, and polycyclooctene diol; wherein the polyhedral oligosilsesquioxane diol is a member selected from the group consisting of 2-ethyl-2-[3-[[(heptacyclopentyl-pentacyclo-[9.5.1.1$^{3,9}$.1$^{5,15}$.1$^{7,13}$]octasiloxanyl)oxy[dimethylsilyl]-propoxy]methyl]-1,3-propanediol, 2-ethyl-2-[3-[[(heptacyclohexylpentacyclo-]9.5.1.1$^{3,9}$.1$^{5,15}$.1$^{7,13}$]octasiloxanyl)oxy]dimethylsilyl]-propoxy]methyl]-1,3-propanediol, 2-ethyl-2-[3-[[(heptaisobutylpentacyclo-[9.5.1.1$^{3,9}$.1$^{7,13}$]octasiloxanyl)oxy]dimethylsilyl]-propoxy]methyl]-1,3-propanediol, 1-(2-trans-cyclohexanediol) ethyl-3,5,7,9,11,13,15-cyclohexanepentacyclo-[9.5.1.1$^{3,9}$.1$^{5,15}$.1$^{7,13}$]octasiloxane, and 1-(2-trans-cyclohexanediol) ethyl-3,5,7,9,11,13,15-isobutylpentacyclo-[9.5.1.1$^{3,9}$.1$^{5,15}$.7$^{,13}$]octasiloxane; and wherein the diisocyanate is 4,4'-diphenyl methylene diisocyanate.

11. The method of claim 10 wherein said reaction is carried out in presence of dibutyltin dilaurate as catalyst.

12. A method for making a thermoplastic polyurethane shape memory polymer comprising reacting in one step (A) a polyol, (B) a polyhedral oligosilsesquioxane diol, and (C) a diisocyanate, wherein the polyol is polyethylene glycol, wherein the polyhedral oligosilsesquioxane is 1-(2-trans-cyclohexanediol)ethyl-3,5,7,9,11,13,15-isobutylpentacyclo-[9.5.1.1$^{3,9}$.1$^{5,15}$.1$^{7,13}$]octasiloxane, and wherein the diisocyanate is 4,4'-diphenyl methylene diisocyanate.

13. A method for making a thermoplastic polyurethane shape memory polymer comprising reacting in one step (A) a polyol, (B) a polyhedral oligosilsesquioxane diol, and (C) a diisocyanate, wherein the polyol is polycyclooctene diol, wherein the polyhedral oligosilsesquioxane diol is 2-ethyl-2-[3-[[(heptaisobutylpentacyolo-[9.5.1.1$^{3,9}$.1$^{5,15}$.1$^{7,13}$]octasiloxanyl)oxy]dimethytsilyl]-propoxy]methyl]-1,3-propanediol, and wherein the diisocyanate is 4,4'-diphenyl methylene diisocyanate.

14. A thermoplastic polyurethane shape memory polymer prepared by the method of claim 10.

15. A thermoplastic polyurethane shape memory polymer prepared by the method of claim 11.

16. A thermoplastic polyurethane shape memory polymer prepared by the method of claim 11.

17. A thermoplastic polyurethane shape memory polymer prepared by the method of claim 13.

18. A thermoplastic polyurethane shape memory polymer prepared by a method comprising reacting in one step (A) a polyol, (B) a polyhedral oligosilsesquioxane diol, and (C) a diisocyanate, wherein the thermoplastic polyurethane shape memory polymer exhibits a thermal triggering temperature of 30 to 60° C.

19. The thermoplastic polyurethane shape memory polymer of claim 18, wherein the thermoplastic shape memory polymer exhibits a thermal triggering temperature of 37° C. to 50° C.

20. A thermoplastic polyurethane shape memory polymer having the formula

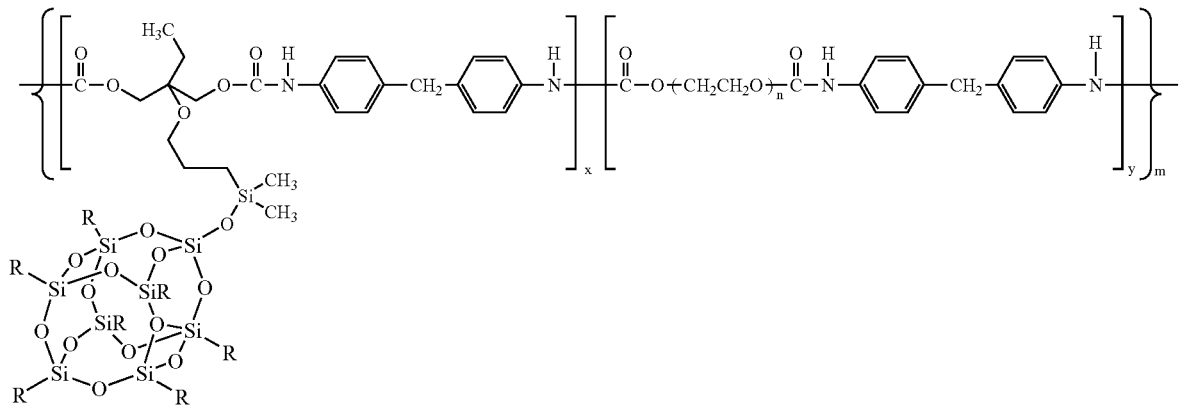

wherein R is isobutyl, wherein the ratio of x:y is 1 to 20, the polyol degree of polymerization is 1<n<1000 and the total degree of polymerization, 2<m<100.

* * * * *

UNITED STATES PATENT AND TRADEMARK OFFICE
CERTIFICATE OF CORRECTION

PATENT NO.         : 7,091,297 B2
APPLICATION NO.    : 10/683167
DATED              : August 15, 2006
INVENTOR(S)        : Mather et al.

It is certified that error appears in the above-identified patent and that said Letters Patent is hereby corrected as shown below:

<u>In The Drawings:</u> delete Figures 1-5 and substitute therefor attached Figures 1-4

<u>Column 3:</u> Line 14 and 15, after "a" delete "dilisocyante" and insert therefor --diisocyanate--
Line 38, before "(MDI)" delete "dilsocyanate" and insert therefor --diisocyanate--

<u>Column 7:</u> Line 46, after "Aqueous" delete "Theological" and insert therefor --rheological--

Signed and Sealed this

Nineteenth Day of December, 2006

JON W. DUDAS
*Director of the United States Patent and Trademark Office*

DMA plots of the TMP POSS based TPU, with mole ratio of PEG : POSS as 1:6, 1:4 respectively. A transition temperature around 45-47°C was observed. A typical plateau corresponding to physically crosslinked polymers was observed also.

-A- PEG : POSS = 1:3
-B- PEG : POSS = 1:4
-C- PEG : POSS = 1:6
-D- PEG : POSS = 1:8

DSC results of TMP POSS based TPU with different PEG : POSS mole ratio. Two melting peaks can be observed indicating the microphase separation between the soft and hard segment.

Stress-strain experiment of the TMP POSS based TPU (PEG : POSS = 1:6) according to ASTM standard. A dumbbell shaped sample having the length of the narrow part as 9.42 mm, distance between grips as 25.5 mm and thickness as 0.355 mm was stretched at room temperature, 1 mm/min.